United States Patent
Kang et al.

(10) Patent No.: US 8,623,927 B2
(45) Date of Patent: Jan. 7, 2014

(54) CATALYST FOR SYNTHESIZING METHANOL FROM SYNTHESIS GAS AND PREPARATION METHOD THEREOF

(75) Inventors: Suk-Hwan Kang, Daejeon (KR); Jong Wook Bae, Daejeon (KR); Ki Won Jun, Daejeon (KR); Keh-Sik Min, Seoul (KR); Seok-Lyong Song, Ulsan (KR); Sam-Heon Jeong, Ulsan (KR)

(73) Assignees: Hyundai Heavy Industries Co., Ltd., Ulsan (KR); Korea Research Institute of Chemical Technology, Daejeon (KR)

( * ) Notice: Subject to any disclaimer, the term of this patent is extended or adjusted under 35 U.S.C. 154(b) by 340 days.

(21) Appl. No.: 13/055,496

(22) PCT Filed: Jul. 24, 2009

(86) PCT No.: PCT/KR2009/004128
§ 371 (c)(1),
(2), (4) Date: Jan. 24, 2011

(87) PCT Pub. No.: WO2010/011101
PCT Pub. Date: Jan. 28, 2010

(65) Prior Publication Data
US 2011/0118367 A1    May 19, 2011

(30) Foreign Application Priority Data
Jul. 24, 2008  (KR) .................. 10-2008-0072286

(51) Int. Cl.
*C07C 27/00* (2006.01)
(52) U.S. Cl.
USPC ............................ 518/714; 518/700; 518/713
(58) Field of Classification Search
USPC .......................................... 518/700, 713, 714
See application file for complete search history.

(56) References Cited

U.S. PATENT DOCUMENTS

| | | | |
|---|---|---|---|
| 4,483,943 A | 11/1984 | Windawi et al. | |
| 4,835,132 A | 5/1989 | Sambrook | |
| 4,843,101 A | 6/1989 | Klier et al. | |
| 5,221,652 A | 6/1993 | Tierney et al. | |
| 5,254,520 A | 10/1993 | Sofianos | |
| 6,054,497 A | 4/2000 | Sofianos et al. | |
| 6,342,538 B1 | 1/2002 | Matsumura et al. | |
| 2009/0048355 A1 | 2/2009 | Polier et al. | |

FOREIGN PATENT DOCUMENTS

| | | | |
|---|---|---|---|
| CN | 1891337 A | | 1/2007 |
| EP | 0 742 193 A1 | | 11/1996 |
| GB | 1159035 A | | 7/1969 |
| JP | 09141099 | * | 6/1997 |
| JP | 10216522 | * | 8/1998 |
| JP | 2002-60357 A | | 2/2002 |
| KR | 10-2008-0011628 A | | 2/2008 |
| WO | WO 2006/117190 A1 | | 11/2006 |

OTHER PUBLICATIONS

Wender, Irving, "Reactions of Synthesis Gas", Fuel Processing Technology 48 (1996), pp. 189-297.
Chinchen, G.C. et al., "The Activity and State of the Copper Surface in Methanol Synthesis Catalysts", Applied Catalysis, 25 (1986), pp. 101-107.
Jingfa, Deng et al., "A Novel Process for Preparation of a Cu/ZnO/ $Al_2O_3$ Ultrafine Catalyst for Methanol Synthesis from $CO_2 + H_2$: Comparison of Various Preparation Methods", Applied Catalysis A: General; 139 (1996), pp. 75-85.

* cited by examiner

*Primary Examiner* — Jafar Parsa
(74) *Attorney, Agent, or Firm* — Dickstein Shapiro LLP

(57) ABSTRACT

Disclosed are a catalyst for synthesis of methanol from synthesis gas and a method for preparing the same. The catalyst includes a Cu—Zn—Al oxide containing CuO, ZnO and $Al_2O_3$ in a predetermined ratio or Cu—Zn—Al—Zr oxide containing CuO, ZnO, $Al_2O_3$ and $ZrO_2$ in a predetermined ratio, in combination with a cerium-zirconium oxide obtained by a sol-gel process. As compared to the existing Cu—Zn—Al catalysts for synthesizing methanol, the catalyst disclosed herein inhibits formation of byproducts and improves yield of methanol. Therefore, it is possible to improve methanol purification efficiency and carbon conversion efficiency.

6 Claims, 1 Drawing Sheet

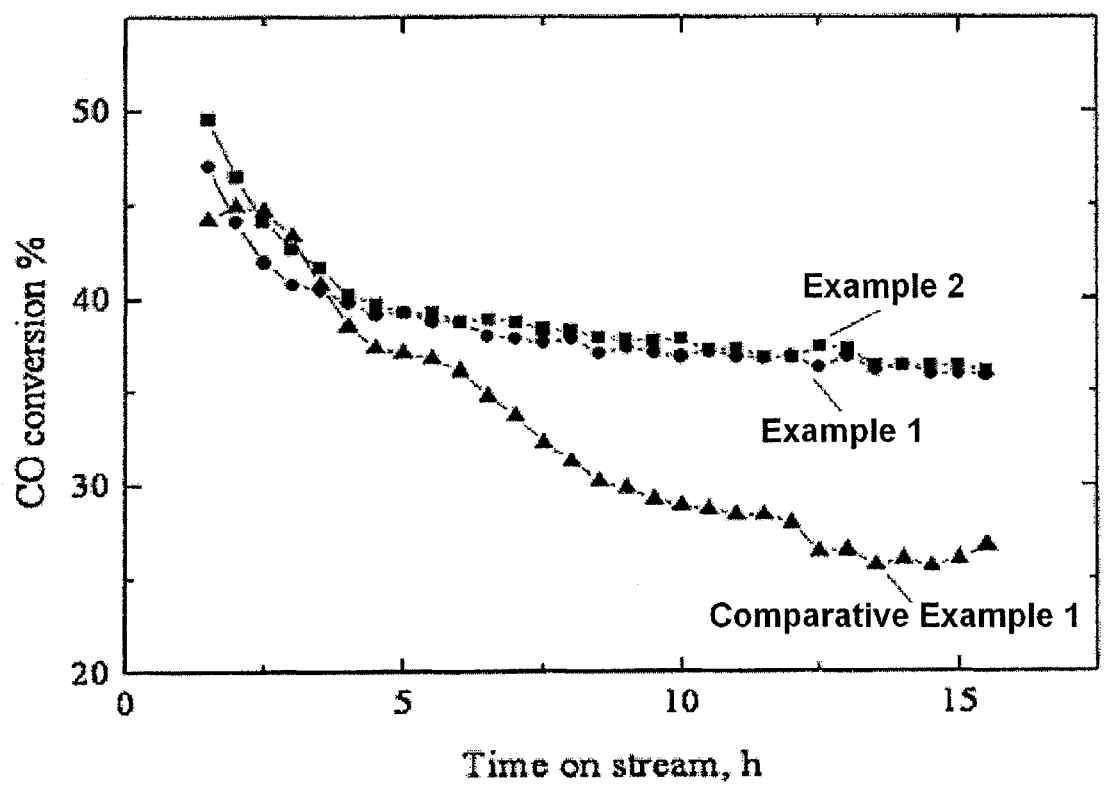

CATALYST FOR SYNTHESIZING METHANOL FROM SYNTHESIS GAS AND PREPARATION METHOD THEREOF

TECHNICAL FIELD

The present disclosure relates to a catalyst for use in synthesizing methanol from synthesis gas, including a Cu—Zn—Al oxide and a predetermined amount of cerium-zirconium oxide as an admixture, and a method for preparing the same catalyst.

BACKGROUND ART

In general, industrially applicable processes for synthesizing methanol, which is an important starting material for petrochemical materials, include use of synthesis gas produced through the gasification of coal or biomass and reforming of natural gas. Such gasification of coal or biomass generally uses a fluidized-bed reactor, and requires a dust collection system for collecting dust as well as removal systems of sulfur compounds or nitrogen oxides contained in raw materials. Therefore, methanol has been produced mostly (70% or more) by a commercial process using synthesis gas obtained from the reforming of natural gas. In Korea, methanol is in demand of about 1.2 million tons/year, is used in synthetic resins, chemical fiber materials, methyl t-butyl ether (MTBE), acetic acid, etc., and costs $250-500/ton variably.

The annual production capacity of methanol reaches 20 million tons all over the world. However, when methanol partially substitutes for gasoline or diesel fuel, it is expected that methanol is increasingly in demand. In addition, methanol as liquid fuel emits a lower amount of harmful nitrogen oxides (NOx) as compared to gasoline or diesel fuel, and thus it is expected that such high eco-friendly characteristics of methanol results in industrial demand as a fuel substitute. Currently, high cost of methanol limits its use as a fuel substitute. However, due to the recent tendency of high oil price, commercial use of methanol as a non-petroleum fuel substitute has been spotlighted.

Methanol is produced from synthesis gas via the hydrogenation of carbon monoxide or carbon dioxide as depicted in the following reaction formulae:

$$CO + 2H_2 \leftrightarrow CH_3OH \quad \Delta H = -90.8 \text{ kJ/mol} \quad (1)$$

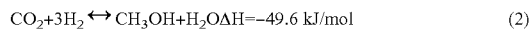

$$CO_2 + 3H_2 \leftrightarrow CH_3OH + H_2O \quad \Delta H = -49.6 \text{ kJ/mol} \quad (2)$$

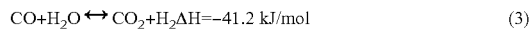

$$CO + H_2O \leftrightarrow CO_2 + H_2 \quad \Delta H = -41.2 \text{ kJ/mol} \quad (3)$$

Reaction formulae (1) and (2) are kinds of the exothermic volume-reducing reactions, and thus they prefer a low temperature and a high pressure thermodynamically. However, since reaction rate increases in proportion to temperature, industrial production of methanol has been conducted at an adequate temperature. Due to this, an actual commercialized process is operated under a one-pass conversion of reaction gases of 15-25% in order to prevent accumulation of reaction heat. Because of such a low one-pass conversion of methanol, the production cost increases. Meanwhile, the unreacted gases are recirculated and this results in an additional need for a system for synthesizing methanol. If a reaction is carried out according to reaction formula (2) to produce water, a water gas shift reaction (WGS), such as one as shown in reaction formula (3), occurs as a side reaction, thereby forming surplus hydrogen and increasing reaction rate of methanol synthesis.

When using synthesis gas, the types of chemicals produced by the reaction vary significantly depending on the particular reaction process and catalyst type. For example, in the case of the Sasol process (South Africa), using an iron-based catalyst in a fluidized-bed reactor results in production of gasoline (*Fuel. Pro. Tech.* 48 (1996) 189), while using a Cu/Zn/Al catalyst in a fixed-bed reactor results in facile production of methanol as an important starting chemical. To perform such reactions, as a methanol synthesis catalyst for high-pressure application, BASF Corporation (Germany) has developed a zinc chromate-based catalyst. As a catalyst for low-pressure application, a Cu—based catalyst has been developed. However, such catalysts are susceptible to poisoning with 1 ppm of sulfur compounds. Since an improved catalyst for methanol synthesis has been disclosed by ICI Co. in 1996, various companies have developed high-quality catalysts. Some industrially applicable catalysts for methanol synthesis are summarized in Table 1.

TABLE 1

Chemical composition of catalysts for methanol synthesis according to related art

| Production Co. | Catalyst system | Composition |
|---|---|---|
| Ammonia Casale | Cu—Zn—Al—Cr | 29:47:6:18 |
| BASF | Cu—Zn—Al | 32:42:26 |
|  | Cu—Zn—Al—Cr—Mn | 38:38:0.4:12:12 |
| Dupont | Cu—Zn—Al | 50:19:31 |
| Halder Topsoe | Cu—Zn—Cr | 37:15:48 |
| ICI | Cu—Zn—Al | 61:30:9 |
|  | Cu—Zn—Al | 64:23:13 |
| Lurgi | Cu—Zn—V | 61:30:9 |
|  | Cu—Mn—V | 48:30:22 |
| Mitsubishi Gas Chemical | Cu—Zn-Mp | 55:43:2 |
|  | Cu—Zn—Cr | 55:43:2 |
|  | Cu—Zn—B | 61:38:1 |
| Shell | Cu—Zn—Ag | 61:24:15 |
|  | Cu—Zn—RE | 71:24:5 |
| United Catalysis | Cu—Zn—Al | 62:21:7 |

The catalysts developed for low-pressure application use Cu and Zn as main catalyst components and Al or Cr as a co-catalyst component. Currently, a catalyst available from ICI and having a molar ratio of Cu/Zn/Al of 60/30/10 has been used widely. In 1960's, ICI has developed a process for synthesizing methanol from synthesis gas obtained from coal on a ternary catalyst (Cu/Zn/Al$_2$O$_3$) at a reaction temperature of 230-280° C. under a pressure of 50-100 atm. Particularly, a currently industrialized process for synthesizing methanol is operated on a Cu/Zn/Al$_2$O$_3$ catalyst at a reaction temperature of 250° C. under a pressure of 50-100 atm by using synthesis gas (CO/CO$_2$/H$_2$) obtained by steam reforming of natural gas.

In addition to the above, other catalysts for methanol preparation are also reported, and particular examples thereof include: catalysts obtained by co-precipitation of metals in slurry (U.S. Pat. No. 5,221,652; EP 07421193 A1); methanol preparation catalyst systems containing components, such as Cu—Zn—Zr (U.S. Pat. No. 6,504,497), Cu—Zn—Al—Ga (Japanese Laid-Open Patent No. 2002-60357) or Cu—Zn—Al—Zr—Mo (U.S. Pat. No. 5,254,520) modified from the known Cu—Zn—Al; or the like. Further, U.S. Pat. No. 6,342,538 discloses a Pd/CeO$_2$ catalyst system free from Cu and Zn and using ceria with a particle size of 5 nm or less as a carrier.

The synthesis gas suitable for methanol synthesis has a H$_2$/(2CO+3CO$_2$) ratio of about 1.05. Since the yield of methanol increases in proportion to the ratio, it is required to add hydrogen or to remove carbon dioxide to adjust the ratio.

Although many workers have participated in studies for improving the performance of methanol synthesis catalysts, understanding about the active sites of a catalyst for methanol synthesis is not completely accomplished. However, it is known that oxidation state of Cu and redox property of reduced Cu particles play an important role in determining the catalytic activity. It is also known that the activity of a Cu catalyst in a reaction of methanol synthesis is in proportion to the specific surface area of metallic Cu component. It is reported that coordination, chemisorption and activation of CO and homogeneous $H_2$ splitting occur on $Cu^0$ or $Cu^+$, and non-homogeneous $H_2$ splitting, leading to $H^{\delta+}$ and $H^{\delta-}$ in a catalytic system using a ZnO—containing catalyst, occurs on ZnO (*Appl. Catal. A* 25, (1986) 101). Herein, it is reported that when the molar ratio of Cu/Zn is 8 or more, the specific surface area decreases rapidly (*Appl. Catal. A* 139, (1996) 75). For this reason, Cu is used in combination with Zn to prepare the catalyst, and a molar ratio of Cu/Zn of 3/7 is known to provide the highest activity. However, it is known that when $CO_2$ is present or when the proportion of oxygen-containing materials that cover the $Cu^0$ surface increases, the catalyst activity is independent from the $Cu^0$ surface area. It is reported that such a phenomenon results from the fact that the $Cu^+$ active site functions as an active site during the methanol synthesis.

To obtain a catalyst for methanol synthesis, ZnO, $ZrO_2$, $Cr_2O_3$ and $SiO_2$ are used as carriers or promoters. In the case of ZnO, $Zn^+$ ions are arranged at the site of tetrahedron by $O^{2-}$ ions, and ZnO serves to optimize dispersion of Cu particles in a Cu—based catalyst and to stabilize the active site. ZnO itself also acts as a catalyst for hydrogenation.

When using a catalyst containing a simple mixture of $Cu/SiO_2$ and $ZnO/SiO_2$, ZnO does not serve to deform the shape of Cu sites but contribute to formation of Cu—Zn active sites. In this context, ZnO causes a change in electrical properties of Cu sites by the interaction with Cu particles and electron exchange.

Considering that high-petroleum price is to be maintained continuously in the future, it is expected that there is a rapid increase in utility of methanol as a fuel substitute or reactant for fuel cells. Under these circumstances, it is quite necessary to develop a catalyst system for carrying out an efficient reaction by which methanol is produced from synthesis gas in a cost-efficient manner.

In addition, there have been problems in the related art that generation of carbon dioxide caused by oxidation of carbon monoxide occurring as one of the side reactions on the catalysts for methanol synthesis, as well as generation of hydrocarbons and DME leads to a drop in yield of methanol.

DISCLOSURE

Technical Problem

It is now well demonstrated that a novel catalyst system, including a Cu—Zn—Al oxide containing CuO, ZnO and $Al_2O_3$ in a predetermined ratio or Cu—Zn—Al—Zr oxide containing CuO, ZnO, $Al_2O_3$ and $ZrO_2$ in a predetermined ratio, in combination with a cerium-zirconium oxide obtained by a sol-gel process, is capable of increasing the carbon availability in a reaction for methanol synthesis and improving the efficiency in the subsequent operation for separating a desired product.

The present disclosure is directed to providing a catalyst for methanol synthesis obtained by incorporating a Cu—Zn—Al oxide or Cu—Zn—Al—Zr oxide to a cerium-zirconium oxide as an admixture, and a method for preparing the same.

The present disclosure is also directed to providing a process for synthesizing methanol using the same catalyst.

Technical Solution

In one aspect, there is provided a catalyst for methanol synthesis, which is obtained by incorporating a Cu—Zn—Al oxide or Cu—Zn—Al—Zr oxide to a cerium-zirconium oxide as an admixture.

In another aspect, there is provided a method for preparing the catalyst.

The catalyst disclosed herein allows methanol synthesis from synthesis gas containing carbon monoxide and hydrogen. More particularly, the catalyst includes a Cu—Zn—Al oxide or Cu—Zn—Al—Zr oxide as a catalyst for methanol synthesis, and a cerium-zirconium oxide as an admixture obtained by a sol-gel process in a predetermined amount.

The method for preparing a catalyst based on Cu—Zn—Al or Cu—Zn—Al—Zr for use in methanol synthesis from synthesis gas disclosed herein includes:

preparing a cerium-zirconium oxide having a specific surface area of 100-300 $m^2/g$ by a sol-gel process, and firing the cerium-zirconium oxide at a temperature of 100-600° C. to provide an admixture for methanol synthesis; and adding a metal mixture of a copper precursor, zinc precursor and alumina precursor or a metal mixture of a copper precursor, zinc precursor, alumina precursor and zirconium precursor, and a basic precipitating agent to aqueous suspension containing the cerium-zirconium oxide, carrying out co-precipitation in an aqueous solution with a pH of 7-8 and aging the resultant precipitate, followed by filtering and washing, and firing the precipitate at a temperature of 200-600° C.

To incorporate a Cu—Zn—Al oxide or Cu—Zn—Al—Zr oxide to a cerium-zirconium oxide obtained by a sol-gel process, the cerium-zirconium oxide may be obtained by the method as described hereinafter.

More particularly, the method for preparing a cerium-zirconium oxide as an admixture includes:

adding a cerium precursor and a zirconium precursor dissolved in water to a solution of citric acid and ethylene glycol;

agitating the resultant mixture at 50-100° C. and heating the mixture for 5-10 hours at 120-130° C. to remove water contained in the solution completely, thereby providing a sol;

maintaining the resultant sol at 100° C., 150° C., 200° C. and 300° C., each for 0.5-2 hours, at a heating rate of 3-7° C./min, and at 400° C. for 2-10 hours, followed by firing at 500° C. for 3-5 hours.

According to an embodiment, the process for synthesizing methanol from synthesis gas by using the catalyst obtained as described above is carried out as follows. The catalyst is used for a catalytic reaction after it is reduced at a zone of 200-500° C. in a fixed-bed reactor under hydrogen atmosphere. The reduced hybrid catalyst is used under reaction conditions similar to those of general methanol synthesis carried out in a fixed-bed reactor. More particularly, the catalytic reaction may be carried out at a reaction temperature of 200-400° C., under a reaction pressure of 30-60 $kg/cm^2$, with a space velocity of 1000-10000 $h^{-1}$.

Advantageous Effects

As mentioned above, the catalyst disclosed herein is a mixed catalyst system including a Cu—Zn—Al oxide based on CuO, ZnO and $Al_2O_3$ or Cu—Zn—Al—Zr oxide based on CuO, ZnO, $Al_2O_3$ and $ZrO_2$, in combination with a cerium-zirconium oxide obtained by a sol-gel process in a predetermined amount. When the catalyst is used in a reaction for methanol synthesis, it is possible to prepare high-purity methanol directly from synthesis gas, while inhibiting production of byproducts, such as DME, hydrocarbons and carbon dioxide. Therefore, it is possible to increase yield of methanol based on one-pass conversion as compared to known classes of catalysts, resulting in an increase in carbon availability and improvement of efficiency in the subsequent process for separating a desired product. Further, the use of a cerium-zirconium oxide as an admixture for preparing the catalyst improves the stability of the catalyst during a process for synthesizing methanol through the conversion of synthesis gas.

DESCRIPTION OF DRAWINGS

FIG. 1 is a graph illustrating the CO conversion and catalyst stability as a function of reaction time, when using each of the catalysts for synthesizing methanol from synthesis gas, obtained from Examples 1 and 2 and Comparative Example 1.

MODE FOR INVENTION

In some embodiments, there are provided a catalyst for methanol synthesis, which is obtained by incorporating a Cu—Zn—Al oxide or Cu—Zn—Al—Zr oxide to a cerium-zirconium oxide as an admixture, and a method for preparing the same.

Hereinafter, the catalyst and the method will be explained in more detail.

The catalyst disclosed herein is applicable to synthesis of methanol from synthesis gas including carbon monoxide and hydrogen. Particularly, the catalyst includes a Cu—Zn—Al oxide or Cu—Zn—Al—Zr oxide as a catalyst for methanol synthesis, in combination with a cerium-zirconium oxide as an admixture obtained by a sol-gel process in a predetermined amount. As compared to the known catalyst, Cu—Zn—Al, for methanol synthesis, the catalyst disclosed herein shows higher activity, stability and one-throughput yield of methanol during a reaction for methanol synthesis and has excellent long-term stability and quality, while inhibiting formation of byproducts, such as DME, carbon dioxide and hydrocarbons.

The catalyst disclosed herein has a specific surface area of 50-250 $m^2/g$. The specific surface area may be 80-200 $m^2/g$. When the catalyst has a specific surface area less than 50 $m^2/g$, pores in cerium-zirconium oxide may be blocked by Cu—Zn—Al oxide so that Cu dispersibility decreases and active sites are reduced, resulting in a drop in conversion into methanol. When the catalyst has a specific surface area higher than 250 $m^2/g$, stability of Cu—Zn—Al oxide participating in the reaction for methanol synthesis is lowered and active sites available for the reaction for methanol synthesis are reduced, resulting in a drop in conversion of carbon monoxide.

The Cu—Zn—Al oxide or Cu—Zn—Al—Zr oxide included in the catalyst disclosed herein has been used widely as a catalyst for methanol synthesis. Cerium and zirconium have been used widely as carriers in the form of their oxides or as additives to be mixed with precursors for preparing the catalyst. However, the catalyst disclosed herein is not derived from simple physical mixing of the known catalyst with additives but is a novel catalyst formed from a chemical reaction, wherein the cerium-zirconium oxide used as an admixture is obtained by a sol-gel process.

The catalyst including a Cu—Zn—Al oxide or Cu—Zn—Al—Zr oxide in combination with a cerium-zirconium oxide in a predetermined amount shows improved Cu dispersion favorable to methanol synthesis, thereby improving selectivity to methanol while inhibiting formation of byproducts, such as DME, hydrocarbons and carbon dioxide.

In some embodiments, there is provided a method for preparing a catalyst based on Cu—Zn—Al or Cu—Zn—Al—Zr for use in methanol synthesis from synthesis gas, the method including:

preparing a cerium-zirconium oxide having a specific surface area of 100-300 $m^2/g$ by a sol-gel process, and firing the cerium-zirconium oxide at a temperature of 100-600° C. to provide an admixture for methanol synthesis; and adding a metal mixture of a copper precursor, zinc precursor and alumina precursor or a metal mixture of a copper precursor, zinc precursor, alumina precursor and zirconium precursor, and a basic precipitating agent to aqueous suspension containing the cerium-zirconium oxide, carrying out co-precipitation in an aqueous solution with a pH of 7-8 and aging the resultant precipitate, followed by filtering and washing, and firing the precipitate at a temperature of 200-600° C.

To incorporate the catalyst for methanol synthesis based on Cu—Zn—Al or Cu—Zn—Al—Zr to a cerium-zirconium oxide as an admixture obtained by a sol-gel process, the cerium-zirconium oxide may be obtained by the method described hereinafter.

In other words, the method for preparing a cerium-zirconium oxide as an admixture includes:

adding a cerium precursor and a zirconium precursor dissolved in water to a solution of citric acid and ethylene glycol;

agitating the resultant mixture at 50-100° C. and heating the mixture for 5-10 hours at 120-130° C. to remove water contained in the solution completely, thereby providing a sol;

maintaining the resultant sol at 100° C., 150° C., 200° C. and 300° C., each for 0.5-2 hours, at a heating rate of 3-7° C./min, and at 400° C. for 2-10 hours, followed by firing at 500° C. for 3-5 hours.

In the cerium-zirconium metal oxide obtained by a sol-gel process, the metals may be present in a weight ratio of 0.02<Ce/Zr<0.5. When the weight ratio of Ce/Zr metals is less than 0.02, acid sites in $ZrO_2$ increase in amount, resulting in an increase in selectivity to byproducts, such as DME. When the weight ratio of Ce/Zr metals is higher than 0.5, acid sites and base sites facilitating formation of byproducts increase in amount, thereby increasing formation of byproducts, such as DME and hydrocarbons. Therefore, it is required to maintain the weight ratio of Ce/Zr metals at the above-defined range in order to inhibit formation of byproducts.

A typical embodiment of the method for preparing a finished catalyst for methanol synthesis by incorporating Cu—based active ingredients to the cerium-zirconium oxide as an admixture will be explained hereinafter.

First, co-precipitation is carried out by using a copper precursor, zinc precursor and aluminum precursor in the cerium-zirconium oxide obtained by a sol-gel process. Then, the produced catalyst is fired at 250-350° C.

The catalyst for methanol synthesis obtained as described above may have a weight ratio of metal oxides (CuO, ZnO and $Al_2O_3$ or CuO, ZnO, $Al_2O_3$ and $ZrO_2$) to cerium-zirconium oxide ranging from 0.1 to 10. The Cu—Zn—Al metal oxide has a composition of Cu—Zn—Al corresponding to 40-60 wt % of CuO, 20-35 wt % of ZnO and 5-40 wt % of $Al_2O_3$. In addition, the Cu—Zn—Al—Zr metal oxide has a composition of Cu—Zn—Al—Zr corresponding to 40-60 wt % of CuO, 25-35 wt % of ZnO, 5-20 wt % of $Al_2O_3$ and 1-10 wt % of $ZrO_2$. When CuO is present in an amount less than 40 wt %, methanol yield decreases due to a drop in active sites available for methanol synthesis. When CuO is present in an amount higher than 60 wt %, it is difficult to form an adequate catalyst structure with other metals, leading to a drop in reactivity. When ZnO is present in an amount less than 20 wt %, it is difficult to form an adequate porous structure with CuO and $Al_2O_3$. When ZnO is present in an amount higher than 35 wt %, the proportion of active ingredient, CuO decreases, resulting in a drop in reaction rate for methanol synthesis. When $Al_2O_3$ is present in an amount less than 5 wt %, it is difficult to form a structure favorable to the activity of a catalyst for methanol synthesis based on Cu—Zn—Al. When $Al_2O_3$ is present in an amount higher than 40 wt %, active site available for methanol synthesis decreases in amount, thereby reducing reactivity. When $ZrO_2$ added to improve distribution of active site is present in an amount less than 1 wt %, it is difficult to improve dispersion of active ingredients, resulting in insufficient improvement of reactivity. When $ZrO_2$ is present in an amount higher than 10 wt %, active sites decrease in amount, resulting in a drop in reactivity.

In addition, Cu—Zn—Al oxide is present in a weight ratio to cerium-zirconium oxide of 0.1-10. The weight ratio may be 0.5-8. When the weight ratio is less than 0.1, the catalytic activity for methanol synthesis decreases and conversion into $CO_2$ increase, thereby reduces the methanol yield of the overall process. When the weight ratio exceeds 10, Cu dispersion decreases and conversion into methanol also decreases. For this reason, it is required to maintain the weight ratio at the above defined range.

Hereinafter, the method for preparing a catalyst for use in synthesis of methanol from synthesis gas will be explained in more detail.

First, to aqueous suspension containing a cerium-zirconium oxide obtained by a sol-gel process, a metal mixture of a copper precursor, zinc precursor and alumina precursor or a metal mixture of a copper precursor, zinc precursor, alumina precursor and zirconium precursor, and a basic precipitating agent is added. Then, co-precipitation is carried out in an aqueous solution with a pH of 7-8, followed by aging of the resultant precipitate, and the precipitate is filtered and washed.

The metal mixture includes metal precursors, each of which is generally used in the art. Particular examples of such metal precursors include acetates, hydroxides and nitrates.

The cerium-zirconium oxide obtained as described above is mixed with an aqueous solution to provide an aqueous suspension. To the aqueous suspension, the metal mixture and the basic precipitating agent are added. Then, co-precipitation is carried out in an aqueous solution with a pH of 7-8. The basic precipitating agent is generally known to those skilled in the art and particular examples thereof include sodium carbonate ($Na_2CO_3$), potassium carbonate ($K_2CO_3$), ammonium carbonate (($NH_4)_2CO_3$) or sodium hydrogen carbonate ($NaHCO_3$). Herein, when using a cerium-zirconium oxide free from surface incorporation, precursors of one or more metals selected from Group IIA, IVB and lanthanides may be further incorporated.

After the co-precipitation, the precipitate is aged. Such aging may be carried out at 50-90° C. for at least 2-20 hours. The aging time may be 2-15 hours. Such a condition facilitates formation of a Cu—Zn—Al oxide having excellent activity, thereby improving conversion of synthesis gas into methanol. When the aging temperature is below 50° C., it is difficult to form a Cu—Zn—Al catalyst structure for methanol synthesis. When the aging temperature is above 90° C., the particle size of Cu in the Cu—Zn—Al methanol synthesis catalyst increases and resulted in a drop in activity during the reaction. In addition, when the aging time is less than 2 hours, it is not possible to develop the catalyst structure for methanol synthesis sufficiently. When the aging time exceeds 20 hours, particle size of the catalyst increases, active sites decrease in amount, and processing time increases, resulting in poor cost-efficiency.

After the precipitate is washed, it is dried in an oven at 100° C. or higher, particularly 100-150° C., for 12-24 hours, and then fired at 200-500° C., particularly 300-350° C., to provide a catalyst. When the calcination temperature is lower than 200° C., the metal precursors may not be converted into oxide forms and an adequate catalyst structure may not be formed, resulting in a drop in activity. When the calcination temperature exceeds 500° C., sublimation and particle size growth of Cu cause a decrease in active sites, resulting in a significant drop in reaction rate.

The method for synthesizing methanol from synthesis gas by using the prepared catalyst is as follows. The catalyst is reduced at a temperature of 200-500° C. in a fixed-bed reactor under hydrogen atmosphere, before it is applied to a catalytic reaction. The reduced methanol synthesis catalyst is used under reaction conditions similar to those of a general reaction for methanol synthesis in a fixed-bed reactor. Particularly, the reaction is carried out at a temperature of 200-400° C. under a pressure of 30-60 kg/cm$^2$ with a space velocity of 1000-10000 h$^{-1}$. The catalyst for methanol synthesis obtained as described above provides a high yield of methanol from synthesis gas and inhibits formation of byproducts to less than 1.5% based on the total products. In addition, the catalyst provides a significantly improved one-throughput conversion as compared to other known catalysts and improves the efficiency of a reactor for methanol synthesis.

However, the above-described embodiment does not limit the scope of the present disclosure. For example, the catalyst may be used for various reactors carried out in a fixed-bed reactor, fluidized-bed reactor and slurry reactor for synthesizing methanol from synthesis gas.

The examples will now be described. The following examples are for illustrative purposes only and not intended to limit the scope of the present disclosure.

Example 1

A catalyst for use in synthesis of methanol from synthesis gas is obtained via the co-precipitation process as described hereinafter.

As an admixture, cerium-zirconium oxide is obtained by a sol-gel process.

First, 12.06 g of citric acid and 14.32 g of ethylene glycol are dissolved at 60° C. for 30 minutes under agitation. Next, 2.50 g of cerium nitrate hexahydrate (Ce(NO$_3$)$_2$6H$_2$O) as a Ce precursor is dissolved in a minimum amount of deionized water equal to or less than 30 mL so that it is dissolved completely therein, and then the resultant solution is added gradually to the preformed mixture of citric acid with ethylene glycol to provide solution A. Herein, citric acid is used in a molar amount corresponding to 10 times of cerium and ethylene glycol is used in a molar amount corresponding to 40 times of cerium. In the same manner, 213.01 g of citric acid and 252.89 g of ethylene glycol are dissolved at 60° C. for 30 minutes under agitation. Next, 23.56 g of a zirconium (IV) oxychloride octahydrate (ZrCl$_2$O.8H$_2$O) as a Zr precursor is dissolved in 30 mL or less of water so that it is dissolved completely therein, and then the resultant solution is added gradually to the preformed mixture of citric acid with ethylene glycol to provide solution B. Solution A is mixed with solution B and the mixture is agitated at 60° C. for 30 minutes. Then, the resultant solution is heated at 120-130° C. for 5 hours to remove water contained in the solution completely. The obtained sol-like material is maintained at 100° C., 150° C., 200° C. and 300° C., each for 1 hour, at a heating rate of 5° C./min. Then, the material is maintained at 400° C. for 2 hours so that the surface area of the cerium-zirconium oxide may be maximized. Finally, the material is calcined while maintaining the temperature at 500° C. for 4 hours. Herein, the cerium-zirconium oxide includes 8 wt % of Ce and 92 wt % of Zr (on the metal basis), and has a specific surface area of 164.5 m$^2$/g.

Then, 0.8 g of the cerium-zirconium oxide as an admixture obtained as described above in the form of powder is used together with Cu, Zn and Al precursors. As Cu, Zn and Al precursors, 5.51 g of copper acetate monohydrate (Cu(C$_2$H$_3$O$_2$)$_2$.H$_2$O), 3.03 g of zinc acetate dihydrate (Zn(C$_2$H$_3$O$_2$)$_2$.2H$_2$O), and 2.78 g of aluminum nitrate nonahydrate (Al(NO$_3$)$_3$.9H$_2$O) are dissolved in 600 mL of tertiary distilled water to provide a mixed metal solution having a pH of 5.1. In addition, as a precipitating agent, 5.52 g of sodium carbonate dissolved in 600 mL of deionized water is used, wherein the solution has a pH of 10.2.

In a 2000 mL flask, at 70° C., the mixed metal solution and the precipitating agent solution obtained as described above are added gradually to 200 mL of cerium-zirconium oxide slurried in tertiary distilled water at the same time, while maintaining a final pH of 7.5-8.0. Herein, the mixed solution is agitated for about 3 hours at 70° C., and the resultant catalyst (CuZnAl/Ce$_{0.08}$Zr$_{0.90}$O$_x$) is washed with 2000 mL of deionized water three times or more, filtered, and then dried over at least 12 hours at 100° C. to provide a catalyst for use in synthesis of methanol from synthesis gas. The finished catalyst (CuZnAl/Ce$_{0.08}$Zr$_{0.92}$O$_x$) for methanol synthesis has a specific surface area of 94.1 m$^2$/g.

Then, the catalyst is formed into pellets having a size of 1.2 mm-2.0 mm to test the catalytic activity. The catalyst is calcined under air at 300° C. for 5 hours before it is introduced to a reactor. After the calcination, the catalyst has a composition of Cu—Zn—Al oxide of 53.9 wt % of CuO, 27.6 wt % of ZnO and 18.5 wt % of Al$_2$O$_3$ on the metal oxide basis, and Cu—Zn—Al oxide is present in a weight ratio of 5:1 to cerium-zirconium oxide.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/cm$^2$ with a space velocity of 4000 h$^{-1}$ to carry out the reaction. The results obtained by averaging CO conversion and selectivities over a reaction time ranging from 8 hours to 14 hours under the steady-state are shown in Table 2.

Example 2

A catalyst for methanol synthesis is obtained in the same manner as described in Example 1 except that, as Cu, Zn, Al and Zr precursors, 5.88 g of copper acetate monohydrate (Cu(C$_2$H$_3$O$_2$)$_2$.H$_2$O), 3.23 g of zinc acetate dihydrate (Zn(C$_2$H$_3$O$_2$)$_2$.2H$_2$O), 1.38 g of aluminum nitrate nonahydrate (Al(NO$_3$)$_3$.9H$_2$O) and 0.28 g of zirconium (IV) oxychloride octahydrate (ZrCl$_2$O.8H$_2$O) are dissolved in 600 mL of deionized water to provide a mixed metal solution. In addition, as a precipitating agent, 5.43 g of sodium carbonate dissolved in 600 mL of deionized water is used. After the co-precipitation, the resultant precipitate is aged for 3 hours to provide a catalyst (CuZnAlZr/Ce$_{0.08}$Zr$_{0.92}$O$_x$), which, in turn, is filtered, washed, and then fired to obtain a catalyst for use in methanol synthesis. After the firing, the catalyst for methanol synthesis has a composition of Cu—Zn—Al—Zr oxide of 57.6 wt % of CuO, 29.5 wt % of ZnO, 9.2 wt % of Al$_2$O$_3$ and 3.7 wt % of ZrO$_2$ on the metal oxide basis, and Cu—Zn—Al—Zr oxide is present in a weight ratio of 5:1 to cerium-zirconium oxide. The finished catalyst for methanol synthesis has a specific surface area of 123.0 m$^2$/g.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/cm$^2$ with a space velocity of 4000 h$^{-1}$ to carry out the reaction. The results obtained by averaging CO conversion and selectivities over a reaction time ranging from 8 hours to 14 hours under the steady-state are shown in Table 2.

Example 3

A cerium-zirconium oxide obtained by a sol-gel process is used as an admixture in a similar manner to Example 1. However, in this Example, the cerium-zirconium oxide has a different composition of cerium and zirconium.

First, 12.06 g of citric acid and 14.32 g of ethylene glycol are dissolved at 60° C. for 30 minutes under agitation. Next, 2.50 g of cerium nitrate hexahydrate (Ce(NO$_3$)$_2$.6H$_2$O) as a Ce precursor is dissolved in a minimum amount of deionized water equal to or less than 30 mL so that it is dissolved completely therein, and then the resultant solution is added gradually to the preformed mixture of citric acid with ethylene glycol to provide solution A. Herein, citric acid is used in a molar amount corresponding to 10 times of cerium and ethylene glycol is used in a molar amount corresponding to 40 times of cerium. In the same manner, 104.96 g of citric acid and 124.61 g of ethylene glycol are dissolved at 60° C. for 30 minutes under agitation. Then, 11.61 g of a zirconium (IV) oxychloride octahydrate (ZrCl$_2$O.8H$_2$O) as a Zr precursor is dissolved in 30 mL or less of water so that it is dissolved completely therein, and the resultant solution is added gradually to the preformed mixture of citric acid with ethylene glycol to provide solution B. Solution A is mixed with solution B and the mixture is agitated at 60° C. for 30 minutes. Then, the resultant solution is heated at 120-130° C. for 5 hours to remove water contained in the solution completely. The obtained sol-like material is maintained at 100° C., 150° C., 200° C. and 300° C., each for 1 hour, at a heating rate of 5° C./min. Then, the material is maintained at 400° C. for 2 hours so that the surface area of the cerium-zirconium oxide may be maximized. Finally, the material is calcined while maintaining the temperature at 500° C. for 4 hours. Herein, the cerium-zirconium oxide includes 15 wt % of Ce and 85 wt % of Zr (on the metal basis), and has a specific surface area of 115.1 m$^2$/g.

Then, 0.8 g of the cerium-zirconium oxide as an admixture obtained as described above is used together with Cu, Zn and Al precursors in the same manner as described in Example 1. Particularly, as Cu, Zn and Al precursors, 5.51 g of copper acetate monohydrate (Cu(C$_2$H$_3$O$_2$)$_2$.H$_2$O), 3.03 g of zinc acetate dihydrate (Zn(C$_2$H$_3$O$_2$)$_2$.2H$_2$O), and 2.78 g of aluminum nitrate nonahydrate (Al(NO$_3$)$_3$.9H$_2$O) are dissolved in 600 mL of deionized water to provide a mixed metal solution. In addition, as a precipitating agent, 5.52 g of sodium carbonate dissolved in 600 mL of deionized water is used. After the co-precipitation, the resultant precipitate is aged for 3 hours to provide a catalyst (CuZnAl/Ce$_{0.15}$Zr$_{0.85}$O$_x$), which, in turn, is filtered, washed, and then calcined to obtain a catalyst for use in methanol synthesis. After the calcination, the catalyst for methanol synthesis has a composition of Cu—Zn—Al oxide of 53.9 wt % of CuO, 27.6 wt % of ZnO and 18.5 wt % of $Al_2O_3$ on the metal oxide basis, and Cu—Zn—Al oxide is present in a weight ratio of 5:1 to cerium-zirconium oxide. The finished catalyst for methanol synthesis has a specific surface area of 98.4 $m^2/g$.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/$cm^2$ with a space velocity of 4000 $h^{-1}$ to carry out the reaction. The results obtained by averaging CO conversion and selectivities over a reaction time ranging from 8 hours to 14 hours under the steady-state are shown in Table 2.

Example 4

A cerium-zirconium oxide obtained by a sol-gel process is used as an admixture in a similar manner to Example 1. However, in this Example, the cerium-zirconium oxide has a different composition of cerium and zirconium.

First, 12.06 g of citric acid and 14.32 g of ethylene glycol are dissolved at 60° C. for 30 minutes under agitation. Next, 2.50 g of cerium nitrate hexahydrate ($Ce(NO_3)_2.6H_2O$) as a Ce precursor is dissolved in a minimized amount of deionized water equal to or less than 30 mL so that it is dissolved completely therein, and then the resultant solution is added gradually to the preformed mixture of citric acid with ethylene glycol to provide solution A. Herein, citric acid is used in a molar amount corresponding to 10 times of cerium and ethylene glycol is used in a molar amount corresponding to 40 times of cerium. In the same manner, 351.93 g of citric acid and 417.82 g of ethylene glycol are dissolved at 60° C. for 30 minutes under agitation. Then, 38.92 g of a zirconium (IV) oxychloride octahydrate ($ZrCl_2O.8H_2O$) as a Zr precursor is dissolved in 30 mL or less of water so that it is dissolved completely therein, and the resultant solution is added gradually to the preformed mixture of citric acid with ethylene glycol to provide solution B. Solution A is mixed with solution B and the mixture is agitated at 60° C. for 30 minutes. Then, the resultant solution is heated at 120-130° C. for 5 hours to remove water contained in the solution completely. The obtained sol-like material is maintained at 100° C., 150° C., 200° C. and 300° C., each for 1 hour, at a heating rate of 5° C./min. Herein, the material is maintained at 400° C. for 2 hours so that the surface area of the cerium-zirconium oxide may be maximized. Finally, the material is calcined while maintaining the temperature at 500° C. for 4 hours. Herein, the cerium-zirconium oxide includes 5 wt % of Ce and 95 wt % of Zr (on the metal basis), and has a specific surface area of 118.6 $m^2/g$.

Then, 0.8 g of the cerium-zirconium oxide as an admixture obtained as described above is used together with Cu, Zn and Al precursors in the same manner as described in Example 1. Particularly, as Cu, Zn and Al precursors, 5.51 g of copper acetate monohydrate ($Cu(C_2H_3O_2)_2.H_2O$), 3.03 g of zinc acetate dihydrate ($Zn(C_2H_3O_2)_2.2H_2O$), and 2.78 g of aluminum nitrate nonahydrate ($Al(NO_3)_3.9H_2O$) are dissolved in 600 mL of deionized water to provide a mixed metal solution. In addition, as a precipitating agent, 5.52 g of sodium carbonate dissolved in 600 mL of deionized water is used. After the co-precipitation, the resultant precipitate is aged for 3 hours to provide a catalyst ($CuZnAl/Ce_{0.05}Zr_{0.95}O_x$), which, in turn, is filtered, washed, and then calcined to obtain a catalyst for use in methanol synthesis. After the calcination, the catalyst for methanol synthesis has a composition of Cu—Zn—Al oxide of 53.9 wt % of CuO, 27.6 wt % of ZnO and 18.5 wt % of $Al_2O_3$ on the metal oxide basis, and Cu—Zn—Al oxide is present in a weight ratio of 5:1 to cerium-zirconium oxide. The finished catalyst for methanol synthesis has a specific surface area of 93.5 $m^2/g$.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/$cm^2$ with a space velocity of 4000 $h^{-1}$ to carry out the reaction. The results obtained by averaging CO conversion and selectivities over a reaction time ranging from 8 hours to 14 hours under the steady-state are shown in Table 2.

Comparative Example 1

Unlike Example 1, Comparative Example 1 uses no carrier.
As Cu, Zn and Al precursors, 5.92 g of copper acetate monohydrate ($Cu(C_2H_3O_2)_2.H_2O$), 3.25 g of zinc acetate dihydrate ($Zn(C_2H_3O_2)_2.2H_2O$), and 1.85 g of aluminum nitrate nonahydrate ($Al(NO_3)_3.9H_2O$) are dissolved in 600 mL of deionized water to provide a mixed metal solution. In addition, as a precipitating agent, 5.46 g of sodium carbonate dissolved in 600 mL of deionized water is used. After the co-precipitation, the resultant precipitate is aged for 3 hours to provide a catalyst (CuZnAl), which, in turn, is filtered, washed, and then calcined to obtain a catalyst for use in methanol synthesis. After the calcination, the catalyst for methanol synthesis has a composition of Cu—Zn—Al oxide of 58.0 wt % of CuO, 29.6 wt % of ZnO and 12.4 wt % of $Al_2O_3$ on the metal oxide basis. The finished catalyst for methanol synthesis has a specific surface area of 106.9 $m^2/g$.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/$cm^2$ with a space velocity of 4000 $h^{-1}$ to carry out the reaction. The results obtained by averaging CO conversion and selectivities over a reaction time ranging from 8 hours to 14 hours under the steady-state are shown in Table 2.

Comparative Example 2

Unlike Example 1, Comparative Example 2 uses 0.8 g of high-surface area alumina ($Al_2O_3$) having a specific surface area of 350 $m^2/g$, as an admixture. As Cu, Zn, Al and Zr precursors, 5.88 g of copper acetate monohydrate ($Cu(C_2H_3O_2)_2.H_2O$), 3.23 g of zinc acetate dihydrate ($Zn(C_2H_3O_2)_2.2H_2O$), 1.38 g of aluminum nitrate nonahydrate ($Al(NO_3)_3.9H_2O$) and 0.28 g of zirconium (IV) oxychloride octahydrate ($ZrCl_2O.8H_2O$) are dissolved in 600 mL of deionized water to provide a mixed metal solution. In addition, as a precipitating agent, 5.43 g of sodium carbonate dissolved in 600 mL of deionized water is used. After the co-precipitation, the resultant precipitate is aged for 3 hours to provide a catalyst ($CuZnAlZr/Al_2O_3$), which, in turn, is filtered, washed, and then calcined to obtain a catalyst for use in methanol synthesis. After the calcination, the catalyst for methanol synthesis has a composition of Cu—Zn—Al—Zr oxide of 57.6 wt % of CuO, 29.5 wt % of ZnO, 9.2 wt % of $Al_2O_3$ and 3.7 wt % of $ZrO_2$ on the metal oxide basis. In addition, Cu—Zn—Al—Zr oxide is present in a weight ratio of 5:1 to the alumina as an admixture. The finished catalyst for methanol synthesis has a specific surface area of 117.8 $m^2/g$.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/cm² with a space velocity of 4000 h⁻¹ to carry out the reaction. The results obtained by averaging CO conversion and selectivities over a reaction time ranging from 8 hours to 14 hours under the steady-state are shown in Table 2.

Comparative Example 3

Unlike Example 1, Comparative Example 3 uses 0.8 g of zirconia ($ZrO_2$) available from KANTO Co. as an admixture. As Cu, Zn and Al precursors, 5.51 g of copper acetate monohydrate ($Cu(C_2H_3O_2)_2 \cdot H_2O$), 3.03 g of zinc acetate dihydrate ($Zn(C_2H_3O_2)_2 \cdot 2H_2O$), and 2.78 g of aluminum nitrate nonahydrate ($Al(NO_3)_3 \cdot 9H_2O$) are dissolved in 600 mL of deionized water to provide a mixed metal solution. In addition, as a precipitating agent, 5.52 g of sodium carbonate dissolved in 600 mL of deionized water is used. After the co-precipitation, the resultant precipitate is aged for 3 hours to provide a catalyst ($CuZnAl/ZrO_2$), which, in turn, is filtered, washed, and then calcined fired to obtain a catalyst for use in methanol synthesis. After the calcination, the catalyst for methanol synthesis has a composition of Cu—Zn—Al—Zr oxide of 53.9 wt % of CuO, 27.6 wt % of ZnO and 18.5 wt % of $Al_2O_3$ on the metal oxide basis. In addition, Cu—Zn—Al oxide is present in a weight ratio of 5:1 to the zirconia as an admixture. The finished catalyst for methanol synthesis has a specific surface area of 68.4 m²/g.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/cm² with a space velocity of 4000 h⁻¹ to carry out the reaction. The results obtained by averaging CO conversion and selectivities over a reaction time ranging from 8 hours to 14 hours under the steady-state are shown in Table 2.

Comparative Example 4

A cerium-zirconium oxide obtained by a sol-gel process is used as an admixture in a similar manner to Example 1. However, in this Example, the cerium-zirconium oxide has a different composition of cerium and zirconium.

First, 12.06 g of citric acid and 14.32 g of ethylene glycol are dissolved at 60° C. for 30 minutes under agitation. Next, 2.50 g of cerium nitrate hexahydrate ($Ce(NO_3)_2 \cdot 6H_2O$) as a Ce precursor is dissolved in a minimum amount of water equal to or less than 30 mL so that it is dissolved completely therein, and then the resultant solution is added gradually to the preformed mixture of citric acid with ethylene glycol to provide solution A. Herein, citric acid is used in a molar amount corresponding to 10 times of cerium and ethylene glycol is used in a molar amount corresponding to 40 times of cerium. In the same manner, 18.5 g of citric acid and 22.0 g of ethylene glycol are dissolved at 60° C. for 30 minutes under agitation. Then, 2.05 g of a zirconium (IV) oxychloride octahydrate ($ZrCl_2O \cdot 8H_2O$) as a Zr precursor is dissolved in 30 mL or less of water so that it is dissolved completely therein, and the resultant solution is added gradually to the preformed mixture of citric acid with ethylene glycol to provide solution B. Solution A is mixed with solution B and the mixture is agitated at 60° C. for 30 minutes. Then, the resultant solution is heated at 120-130° C. for 5 hours to remove water contained in the solution completely. The obtained sol-like material is maintained at 100° C., 150° C., 200° C. and 300° C., each for 1 hour, at a heating rate of 5° C./min. Then, the material is maintained at 400° C. for 2 hours so that the surface area of the cerium-zirconium oxide may be maximized. Finally, the material is calcined while maintaining the temperature at 500° C. for 4 hours. Herein, the cerium-zirconium oxide includes 50 wt % of Ce and 50 wt % of Zr (on the metal basis), and has a specific surface area of 134.6 m²/g.

Then, 0.8 g of the cerium-zirconium oxide obtained as described above is used together with Cu, Zn and Al precursors in the same manner as described in Example 1. Particularly, as Cu, Zn and Al precursors, 5.51 g of copper acetate monohydrate ($Cu(C_2H_3O_2)_2 \cdot H_2O$), 3.03 g of zinc acetate dihydrate ($Zn(C_2H_3O_2)_2 \cdot 2H_2O$), and 2.78 g of aluminum nitrate nonahydrate ($Al(NO_3)_3 \cdot 9H_2O$) are dissolved in 600 mL of deionized water to provide a mixed metal solution. In addition, as a precipitating agent, 5.52 g of sodium carbonate dissolved in 600 mL of deionized water is used. After the co-precipitation, the resultant precipitate is aged for 3 hours to provide a catalyst ($CuZnAl/Ce_{0.5}Zr_{0.5}O_x$), which, in turn, is filtered, washed, and then fired to obtain a catalyst for use in methanol synthesis. After the calcination, the catalyst for methanol synthesis has a composition of Cu—Zn—Al oxide of 53.9 wt % of CuO, 27.6 wt % of ZnO and 18.5 wt % of $Al_2O_3$ on the metal oxide basis, and Cu—Zn—Al oxide is present in a weight ratio of 5:1 to cerium-zirconium oxide. The finished catalyst for methanol synthesis has a specific surface area of 109.5 m²/g.

Before the reaction is initiated, the catalyst is reduced under hydrogen atmosphere for 4 hours at 250° C. The reactants containing carbon monoxide and hydrogen in a fixed molar ratio of 33.3%:66.7% are introduced to the reactor at a reaction temperature of 250° C. under a pressure of 50 kg/cm² with a space velocity of 4000 h⁻¹ to carry out the reaction. The results obtained by averaging CO conversion and selectivities over a reaction time ranging from 8 hours to 14 hours under the steady-state are shown in Table 2.

TABLE 2

| | CO conversion (mol %) | Product distribution (C-mol %) [MeOH/DME/$CO_2$/others] | Byproducts (yield %)* | Specific surface area (m²/g) |
|---|---|---|---|---|
| Ex. 1 | 36.0 | 96.2/2.4/0.0/1.4 | 1.4 | 94.1 |
| Ex. 2 | 36.1 | 96.2/2.2/0.0/1.6 | 1.4 | 123.0 |
| Ex. 3 | 35.3 | 96.6/2.0/0.0/1.4 | 1.2 | 98.4 |
| Ex. 4 | 35.8 | 96.1/2.7/0.0/1.2 | 1.4 | 93.5 |
| Comp. Ex. 1 | 26.8 | 91.5/3.6/0.0/4.9 | 2.3 | 106.9 |
| Comp. Ex. 2 | 55.3 | 55.0/37.1/6.4/1.5 | 24.9 | 117.8 |
| Comp. Ex. 3 | 39.9 | 90.3/3.5/3.9/2.3 | 3.9 | 68.4 |
| Comp. Ex. 4 | 38.3 | 89.0/7.8/1.2/2.0 | 4.2 | 109.5 |

*Byproducts include DME, $CO_2$ and other chemicals(high-boiling alcohols and hydrocarbons)

As can be seen from Table 2, when using the catalyst obtained by co-precipitation of a Cu—Zn—Al oxide or Cu—Zn—Al—Zr oxide on a cerium-zirconium oxide obtained by a sol-gel process (Examples 1-4) as described above, it is possible to increase selectivity to methanol and stability of the catalyst during a reaction for converting synthesis gas into methanol.

In addition, Comparative Examples 1-4 demonstrate the results obtained from other catalysts for methanol synthesis, using a different kind of admixture other than cerium-zirconium oxide or using no admixture. In the case of Comparative Example 1 using a Cu—Zn—Al catalyst without any admixture, it is shown that carbon dioxide is not formed but a large amount of byproducts are formed, and thus the conversion is very low. Comparative Example 2 provides a catalyst obtained by using high-surface area alumina as an admixture and by adding zirconium upon the co-precipitation. The catalyst of Comparative Example 2 provides a higher conversion as compared to other Examples, because methanol is further subjected to dehydration of methanol to dimethyl ether due to the acid sites of alumina. However, it is not possible to obtain a desired degree of methanol yield due to the formation of a large amount of dimethyl ether and carbon dioxide. Comparative Example 3 provides a catalyst obtained by using zirconia available from KANTO Co. and known as a carrier or additive for methanol synthesis. The catalyst of Comparative Example 3 provides a significantly higher conversion of CO and methanol yield as compared to other Examples. However, it provides a selectivity of 90.3% to methanol, and thus byproducts are formed in a yield of 9.7%. Comparative Example 4 provides a catalyst obtained by using an admixture that has a Ce/Zr weight ratio away from the above-defined range. The admixture used in Comparative Example 4 has a weight ratio of cerium:zirconium of 1:1. In Comparative Example 4, formation of byproducts is increased as compared to other Examples. The catalyst disclosed herein is intended to reduce the yield of DME, carbon dioxide and hydrocarbons generated as byproducts during methanol synthesis to less than 2%, so as to increase the carbon availability and to improve the catalyst stability in a process for synthesizing methanol. Formation of a large amount of byproducts in Comparative Examples 3 and 4 causes loss of reactants, and thus is not suitable for methanol synthesis. It can be seen from the foregoing results that cerium-zirconium oxide may be used sufficiently as an admixture of a catalyst for methanol synthesis, but an excessively high proportion of cerium increases acid sites of the cerium-zirconium oxide, leading to formation of a large amount of byproducts. Therefore, it is necessary to use zirconium and cerium in an adequate amount and weight ratio.

Meanwhile, Examples 1 and 2 use cerium-zirconium oxide as an admixture, wherein the weight ratio of cerium and zirconium is 8:92. In this Examples, adding zirconium as an additive during the co-precipitation increases conversion by 0.1%, while not affecting selectivity to methanol.

FIG. 1 is a graph illustrating the conversion vs. time in the reaction for methanol synthesis using each of the catalysts according to Examples 1 and 2 and Comparative Example 1. As can be seen from FIG. 1, cerium-zirconium oxide as an admixture is shown to increase the catalyst stability.

As can be seen from the foregoing, the catalyst including a Cu—Zn—Al oxide or Cu—Zn—Al—Zr oxide co-precipitated on a cerium-zirconium oxide obtained by a sol-gel process significantly inhibits formation of byproducts, such as hydrocarbon compounds, dimethyl ether and carbon dioxide, as compared to other catalysts using a different kind of admixture or using no metal oxide admixture. In this manner, it is possible to increase the carbon availability in a reaction for methanol synthesis and to reduce the cost required to perform the subsequent separation, thereby improving the efficiency of the overall process.

INDUSTRIAL APPLICABILITY

The catalyst disclosed herein significantly reduces formation of byproducts as compared to the conventional Cu—Zn—Al catalyst systems, thereby increasing carbon availability and efficiency of the subsequent separation and providing excellent long-term quality. As a result, a process for synthesizing methanol from synthesis gas using the catalyst disclosed herein shows high cost-efficiency. The catalyst using a cerium-zirconium oxide obtained by a sol-gel process as an admixture increases one-pass conversion of carbon monoxide used as a reactant, while minimizing formation of byproducts. In this manner, it is possible to reduce the cost required for separation, to increase carbon availability, and thus to realize a highly cost-efficient process for methanol synthesis.

The invention claimed is:

1. A method for synthesizing methanol from synthesis gas comprising:
   using a catalyst for methanol synthesis which comprises a Cu—Zn—Al oxide or Cu—Zn—Al—Zr oxide incorporated with a cerium-zirconium oxide having a metal weight ratio maintained at 0.02<Ce/Zr<0.5 as an admixture, wherein the catalyst for methanol synthesis is prepared by preparing a cerium-zirconium oxide having a specific surface area of 100-300 m2/g by a sol-gel process to provide an admixture for a methanol synthesis catalyst; and
   adding a metal mixture of a copper precursor, zinc precursor and an alumina precursor, and a basic precipitating agent to aqueous suspension containing the cerium-zirconium oxide, carrying out co-precipitation in an aqueous solution with a pH of 7-8 and aging the resultant precipitate, followed by filtering and washing, and calcining the precipitate at a temperature of 200-600° C.

2. The method according to claim 1, which is carried out at a reaction temperature of 200-400° C. under a reaction pressure of 30-60 kg/cm$^2$ with a space velocity of 1000-10000 h$^{-1}$.

3. The method according to claim 1, wherein the Cu—Zn—Al oxide or Cu—Zn—Al—Zr oxide is mixed with the cerium-zirconium oxide in a weight ratio of 0.1-10.

4. The method according to claim 1, wherein the Cu—Zn—Al oxide comprises 40-60 wt % of CuO, 20-35 wt % of ZnO and 5-40 wt % of $Al_2O_3$—; and the Cu—Zn—Al—Zr oxide comprises 40-60 wt % of CuO, 25-35 wt % of ZnO, 5-20 wt % of $Al_2O_3$ and 1-10 wt % of $ZrO_2$.

5. The method according to claim 1, wherein the catalyst has a specific surface area of 50-250 m$^2$/g.

6. The method according to claim 1, wherein the admixture is obtained by a process comprising:
   adding a cerium precursor and a zirconium precursor dissolved in water to a solution of citric acid and ethylene glycol;
   agitating the resultant mixture at a temperature of 50-100° C. and heating the mixture for 5-10 hours at a temperature of 120-130° C. to remove water contained in the solution completely, thereby providing a sol;
   maintaining the resultant sol at 100° C., 150° C., 200° C. and 300° C., each for 0.5-2 hours, at a heating rate of 3-7° C./min, and at 400° C. for 2-10 hours, followed by calcining at 500° C. for 3-5 hours.

* * * * *